| United States Patent [19] | [11] 4,122,175 |
|---|---|
| Schweisguth | [45] Oct. 24, 1978 |

[54] MORPHOLINE CONTAINING BENZIMIDAZOLES

[75] Inventor: Bernard Schweisguth, Meudon, France

[73] Assignee: Hexachimie, Rueil Malmaison, France

[21] Appl. No.: 789,674

[22] Filed: Apr. 21, 1977

[30] Foreign Application Priority Data

Apr. 22, 1976 [GB] United Kingdom ............... 16235/76

[51] Int. Cl.² .................. C07D 265/28; A61K 31/535
[52] U.S. Cl. ............................... 424/248.54; 544/127; 544/139
[58] Field of Search ............................. 544/127, 139; 424/248.54

[56] References Cited

PUBLICATIONS

Dufraisse et al. "Chem. Abstracts" vol. 53 (1959) pp. 1348f – 1349i.

Primary Examiner—Alan L. Rotman
Assistant Examiner—R. W. Ramsuer
Attorney, Agent, or Firm—Fulwider, Patton, Rieber, Lee & Utecht

[57] ABSTRACT

Morpholine derivatives of the formula:

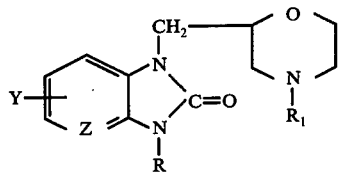

in which Z is CH or N, Y is hydrogen, halogen, alkyl of 1 to 4 carbon atoms, or alkoxy of 1 to 4 carbon atoms, R is hydrogen, alkyl of 1 to 4 carbon atoms, alkenyl of 2 to 4 carbon atoms, benzyl, or phenyl, and $R_1$ is hydrogen or benzyl, and their non-toxic pharmaceutically acceptable acid addition salts have interesting therapeutic properties, especially on the central nervous system.

10 Claims, No Drawings

MORPHOLINE CONTAINING BENZIMIDAZOLES

The present invention relates to morpholine derivatives, to their preparation and to their use in therapy.

The present invention provides, as new compounds, the morpholine derivatives of the formula:

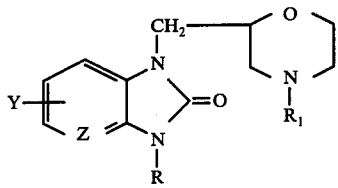

in which Z is CH or N, Y is hydrogen, halogen, alkyl of 1 to 4 carbon atoms, or alkoxy of 1 to 4 carbon atoms, R is hydrogen, alkyl of 1 to 4 carbon atoms, alkenyl of 2 to 4 carbon atoms, benzyl or aryl, especially phenyl, and $R_1$ is hydrogen or benzyl, and their non-toxic, pharmaceutically acceptable acid addition salts, e.g. the hydrochlorides and maleates.

The compounds of formula I in which $R_1$ is benzyl may be prepared by condensing a compound of formula II (preferably in a polar solvent such as hexamethylphosphotriamide, dimethylsulphoxide, or dimethylformamide):

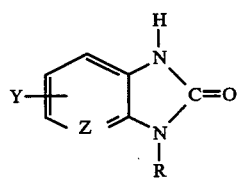

where Z, Y and R are as defined above, which compound has beforehand been metallised by an agent such as a alkali metal alcoholate, alkali metal hydride or alkali metal amide, with a compound of the formula

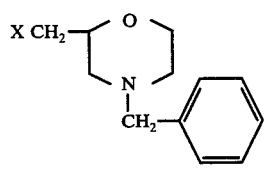

in which X is halogen, preferably chloride.

Catalytic hydrogenation, in an acid medium (for example using palladium on charcoal as catalyst, in an acetic acid medium), of a product prepared in this manner gives a compound of the formula I in which $R_1$ is hydrogen.

The compounds of formulae (II) and (III) may be prepared by procedures described in the literature.

The compounds of formula (I) possess properties which make them valuable in therapy, especially because of their action on the central nervous system, described in more detail below.

The invention includes within its scope pharmaceutical compositions comprising a compound of formula (I) as the base or as a non-toxic acid addition salt together with a therapeutically administrable vehicle or excipient.

The following Examples illustrate the invention.

EXAMPLE 1

4-Benzyl-2-(1-methyl-2,3-dihydro-benzimidazol-2-on-3-yl-methyl)-morpholine (a) 2.6 g (0.11 mol) of sodium hydride are added, in small portions, to 14.8 g (0.1 mol) of 1-methyl-2,3-dihydrobenzimidazol-2-one dissolved in 200 cm³ of dimethylformamide. The mixture is heated at 100° C for 2 hours. 22.5 g (0.1 mol) of 2-chloromethyl-4-benzyl-morpholine dissolved in 50 cm³ of dimethylformamide are added to the reaction mixture. Heating under reflux is continued for 15 hours. The solution is poured into water, made alkaline in the cold and extracted with ether. The organic phase is washed with water until neutral and dried over sodium sulphate. The solvent is evaporated under reduced pressure.

(b) The oil obtained is taken up in ether and treated with a solution of hydrogen chloride in ether until the pH is acid. The hydrochloride precipitates. Recrystallization from isopropanol gives 20 g of 4-benzyl-2-(1-methyl-2,3-dihydro-benzimidazol-2-on-3-yl-methyl)-morpholine hydrochloride, m.p. 190° C.

EXAMPLE 2

2-(1-Methyl-2,3-dihydro-benzimidazol-2-on-3-yl-methyl)-morpholine hydrochloride (a) 20 g (0.05 mol) of 4-benzyl-2-(1-methyl-2,3-dihydro-benzimidazol-2-on-3-yl-methyl)-morpholine hydrochloride are dissolved in 200 cm³ of acetic acid. The product is hydrogenated by stirring (under hydrogen pressure, at ambient temperature) in the presence of palladium on charcoal. Once the theoretical amount of hydrogen has been absorbed, the solution is filtered, rendered alkaline in the cold and extracted with ether. The organic phase is washed with water until neutral and dried over sodium sulphate. The solvent is evaporated under reduced pressure.

(b) The oil obtained is taken up in ether and treated with a solution of hydrogen chloride in ether until the pH is acid. The hydrochloride precipitates. Recrystallization from ethanol gives 10.5 g of 2-(1-methyl-2,3-dihydrobenzimidazol-2-on-3-yl-methyl)-morpholine hydrochloride, m.p. 215° C.

EXAMPLE 3

4-Benzyl-2-(1-benzyl-2,3-dihydro-benzimidazol-2-on-3-yl-methyl)-morpholine hydrochloride.

The condensation of 0.1 mol of 1-benzyl-2,3-dihydrobenzimidazol-2-one and 0.1 mol of 2-chloromethyl-4-benzyl-morpholine is carried out in accordance with the procedure of Example 1. 20 g of 4-benzyl-2-(1-benzyl-2,3-dihydro-benzimidazol-2-on-3-yl-methyl)-morpholine hydrochloride are obtained, m.p. 196° C.

EXAMPLE 4

4-Benzyl-2-(1-methyl-5-methoxy-2,3-dihydro-benzimidazol-2-on-3-yl-methyl)-morpholine hydrochloride The condensation of 0.1 mol of 1-methyl-5-methoxy-2,3-dihydro-benzimidazol-2-one and 0.1 mol of 2-chloromethyl-4-benzyl-morpholine is carried out in accordance with the procedure of Example 1. 18 g of 4-benzyl-2-(1-methyl-5-methoxy-2,3-dihydrobenzimidazol-2-on-3-yl-methyl)-morpholine hydrochloride are obtained, m.p. 175° C.

EXAMPLE 5

4-Benzyl-2-(1-phenyl-2,3-dihydro-imidazo(4,5-b)pyridin-2-on-3-yl-methyl)-morpholine hydrochloride The condensation of 0.1 mol of 1-phenyl-2,3-dihydroimidazo(4,5-b)pyridin-2-one and of 0.1 mol of 2-chloromethyl-4-benzyl-morpholine is carried out in accordance with the procedure of Example 1. Recrystallization of the product from a 50/25 mixture of ethyl acetate and isopropanol gives 19 g of 4-benzyl-2-(1-phenyl-2,3-dihydroimidazo (4,5-b)pyridin-2-on-3-yl-methyl)-morpholine hydrochloride, m.p. 214° C.

EXAMPLE 6

2-(1-Phenyl-2,3-dihydro-imidazo(4,5-b)pyridin-2-on-3-yl-methyl)-morpholine maleate.

19 g of 4-benzyl-2-(1-phenyl-2,3-dihydro-imidazo-(4,5-b)pyridin-2-on-3yl-methyl)-morpholine hydrochloride are treated in accordance with part (a) of Example 2. The oil obtained is dissolved in hot isopropanol. A hot solution of maleic acid in isopropanol is added. The salt precipitates slowly. Recrystallization from isopropanol gives 5 g of 2-(1-phenyl-2,3-dihydro-imidazo-(4,5-b)pyridin-2-on-3-yl-methyl)-morpholine maleate, m.p. 190° C.

EXAMPLE 7

4-Benzyl-2-(1-isopropenyl-2,3-dihydro-benzimidazol-2-on-3-yl-methyl)-morpholine

The condensation of 0.1 mol of 1-isopropenyl-2,3-dihydro-benzimidazol-2-one and 0.1 mol of 2-chloromethyl-4-benzyl-morpholine in accordance with the procedure (a) of Example 1 gives, after evaporation of the solvent under reduced pressure, 30 g of an oil which solidifies slowly. Recrystallization from a 250/25 mixture of isopropyl ether and isopropanol gives 26.5 g of 4-benzyl-2-(1-isopropenyl-2,3-dihydro-benzimidazol-2-on-3-yl-methyl)-morpholine, m.p. 117° C.

EXAMPLE 8

2-1-Isopropyl-2,3-dihydro-benzimidazol-2-on-3-yl-methyl-morpholine 26 g of 4-benzyl-2-(1-isopropenyl-2,3-dihydrobenzimidazol-2-on-3-yl-methyl)-morpholine are treated as in part (a) of Example 2. After evaporation of the solvent under reduced pressure, a limpid oil is obtained, which crystallizes slowly. Recrystallization from isopropyl ether gives 14g of 2-(1-isopropyl-2,3-dihydrobenzimidazol-2-on-3-yl-methyl)-morpholine, m.p. 95° C.

EXAMPLE 9

4-Benzyl-2-(1-phenyl-6-chloro-2,3-dihydrobenzimidazol-2-on-3-yl-methyl)-morpholine hydrochloride The condensation of 0.1 mol of 1-phenyl-6-chloro-2,3-dihydro-benzimidazol-2-one and 0.1 mol of 2-chloromethyl-4-benzyl-morpholine is carried out in accordance with the procedure of Example 1. By washing the product with hot acetone, 28 g of 4-benzyl-2-(1-phenyl-6-chloro-2,3-dihydrobenzimidazol-2-on-3-yl-methyl)-morpholine hydrochloride are obtained, m.p. 185° C.

EXAMPLE 10

2-(1-Phenyl-6-chloro-2,3-dihydro-benzimidazol-2-on-3-yl-methyl)-morpholine maleate 30 g of 4-benzyl-2-(1-phenyl-6-chloro-2,3-dihydro-benzimidazol-2-on-3-yl-methyl)-morpholine hydrochloride are treated as in part (a) of Example 2. After evaporation of the solvent under reduced pressure, 20 g of an oily product are obtained and are dissolved in hot isopropyl alcohol. A hot solution of maleic acid in isopropanol is added. The salt precipitates slowly, 19 g of 2-(1-phenyl-6-chloro-2,3-dihydro-benzimidazol-2-on-3-yl-methyl)-morpholine maleate are obtained, m.p. 234° C.

EXAMPLE 11

4-Benzyl-2-(1-phenyl-2,3-dihydro-benzimidazol-2-on-3-yl-methyl-morpholine

The condensation of 0.1 mol of 1-phenyl-2,3-dihydro-benzimidazol-2-one and 0.1 mol of 2-chloromethyl-4-benzyl-morpholine in accordance with the procedure (a) of Example 1 gives, after evaporation of the solvent under reduced pressure, a pale pink solid which melts at about 90° C and which is used as such for the subsequent operations.

EXAMPLE 12

2-(1-Phenyl-2,3-dihydro-benzimidazol-2-on-3-yl-methyl)-morpholine maleate 18 g of 4-benzyl-2-(1-phenyl-2,3-dihydro-benzimidazol-2-on-3-yl-methyl)-morpholine are treated as in part (a) of Example 2. After evaporation of the solvent under reduced pressure, 15 g of an oily product are obtained and are dissolved in hot isopropyl alcohol. A hot solution of maleic acid in isopropanol is added. The salt precipitates slowly. 16.5 g of 2-(1-phenyl-2,3-dihydro-benzimidazol-2-on-3-yl-methyl)-morpholine maleate are obtained, m.p. 200° C.

The pharmacological activity of the morpholine derivatives according to the invention is illustrated by the following test method.

I. METHOD

Batches of ten male EOPS mice (Iffa Credo strain), weighing 18–20 g each, are given orally the product to be studied. Thirty minutes after the treatment, 30 mg/kg of yohimbine hydrochloride are injected subcutaneously. The mortality is observed 24 hours after injection of yohimbine. The products are administered as an aqueous solution in a volume of 0.5 cm$^3$ per 20 g of body weight. Imipramine is used as the reference compound.

II. RESULTS

The Table which follows shows the percentage of dead animals after 24 hours.

| Example No. mg/kg given orally | 1 | 2 | 3 | 4 | 5 | 8 | 10 | 12 | Imipramine |
|---|---|---|---|---|---|---|---|---|---|
| 0.125 | — | — | — | — | — | — | — | — | 0 |
| 0.5 | — | — | — | — | — | — | — | — | 30 |
| 1 | — | — | — | — | — | — | — | — | — |
| 2 | — | 0 | — | — | 0 | — | 0 | — | 50 |
| 4 | — | — | 0 | — | 20 | 0 | — | 0 | — |
| 8 | — | 30 | — | — | — | — | 20 | — | 60 |
| 16 | 0 | 60 | 20 | 0 | 20 | 20 | — | 20 | — |
| 32 | — | 90 | — | — | — | — | 80 | — | 70 |

-continued

| Example No. mg/kg given orally | 1 | 2 | 3 | 4 | 5 | 8 | 10 | 12 | Imipramine |
|---|---|---|---|---|---|---|---|---|---|
| 64 | 60 | 80 | 40 | 20 | 80 | 60 | — | 60 | 100 |
| 128 | 60 | 100 | 100 | — | — | — | — | — | — |

These results show that the products of the invention exhibit anti-depressant activity. They can be administered to man, e.g. in pills each containing 50 mg, at doses of 50 to 150 mg per day.

I claim:

1. Morpholine derivatives of the formula:

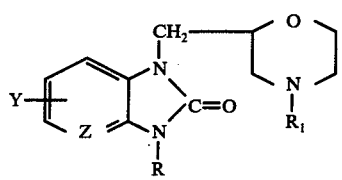

in which Z is CH, Y is hydrogen, halogen, alkyl of 1 to 4 carbon atoms, or alkoxy of 1 to 4 carbon atoms, R is hydrogen, alkyl of 1 to 4 carbon atoms, alkenyl of 2 to 4 carbon atoms, benzyl, or phenyl, and $R_1$ is hydrogen or benzyl, and their non-toxic pharmaceutically acceptable acid addition salts.

2. 4-Benzyl-2-(1-methyl-2,3-dihydro-benzimidazol-2-on-3-yl-methyl)-morpholine and its non-toxic pharmaceutically acceptable acid addition salts.

3. 2-(1-Methyl-2,3-dihydro-benzimidazol-2-on-3-yl-methyl)-morpholine hydrochloride and its non-toxic pharmaceutically acceptable acid addition salts.

4. 4-Benzyl-2-(1-benzyl-2,3-dihydrobenzimidazol-2-on-3-yl-methyl)-morpholine hydrochloride and its non-toxic pharmaceutically acceptable acid addition salts.

5. 4-Benzyl-2-(1-methyl-5-methoxy-2,3-dihydrobenzimidazol-2-on-3-yl-methyl)-morpholine hydrochloride and its non-toxic pharmaceutically acceptable acid addition salts.

6. 2-(1-Isopropyl-2,3-dihydro-benzimidazol-2-on-3-yl-methyl)-morpholine and its non-toxic pharmaceutically acceptable acid addition salts.

7. 2-(1-Phenyl-6-chloro-2,3-dihydro-benzimidazol-2-on-3-yl-methyl)-morpholine maleate and its non-toxic pharmaceutically acceptable acid addition salts.

8. 2-(1-Phenyl-2,3-dihydro-benzimidazol-2-on-3-yl-methyl)-morpholine maleate and its non-toxic pharmaceutically acceptable acid addition salts.

9. A pharmaceutical composition comprising, in association with a therapeutically administrable vehicle or excipient a compound as claimed in claim 1 in an amount effective as an anti-depressant.

10. A method for the therapeutical treatment of depression which comprises the administration of an anti-depressant effective amount of a compound as defined by claim 1.

* * * * *